United States Patent
Levin et al.

(10) Patent No.: US 9,352,134 B2
(45) Date of Patent: May 31, 2016

(54) SEGMENTED BALLOON CATHETER

(71) Applicant: BIOSENSE WEBSTER (ISRAEL) LTD., Yokneam (IL)

(72) Inventors: Michael Levin, Haifa (IL); Yoav Lichtenstein, Raanana (IL); Avi Reuveni, Givat Shmuel (IL); Avigdor Rosenberg, Kiryat Tivon (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 185 days.

(21) Appl. No.: 14/069,729

(22) Filed: Nov. 1, 2013

(65) Prior Publication Data
US 2015/0126882 A1    May 7, 2015

(51) Int. Cl.
| | | |
|---|---|---|
| *A61M 25/10* | (2013.01) |
| *A61B 18/00* | (2006.01) |
| *A61B 18/14* | (2006.01) |
| *A61B 5/0408* | (2006.01) |
| *A61B 18/12* | (2006.01) |

(52) U.S. Cl.
CPC ........ *A61M 25/10185* (2013.11); *A61B 5/0408* (2013.01); *A61B 18/1492* (2013.01); *A61B 18/1206* (2013.01); *A61B 2018/0016* (2013.01); *A61B 2018/0022* (2013.01); *A61B 2018/00267* (2013.01); *A61B 2018/00357* (2013.01); *A61B 2018/00577* (2013.01)

(58) Field of Classification Search
CPC .................. A61M 25/10185; A61M 25/0155; A61B 18/1492; A61B 2018/0022; A61B 2018/0025
See application file for complete search history.

(56) References Cited

U.S. PATENT DOCUMENTS

| | | | | |
|---|---|---|---|---|
| 6,142,993 A | * | 11/2000 | Whayne | A61B 18/1492 600/374 |
| 6,508,784 B1 | | 1/2003 | Shu | |
| 6,656,174 B1 | * | 12/2003 | Hegde | A61B 18/1492 606/159 |
| 7,037,271 B2 | | 5/2006 | Crowley | |
| 2007/0287880 A1 | * | 12/2007 | Ovil | A61M 1/1072 600/16 |

(Continued)

FOREIGN PATENT DOCUMENTS

| | | |
|---|---|---|
| WO | 00/50115 A2 | 8/2000 |
| WO | WO 2005/050115 A2 | 8/2000 |

(Continued)

OTHER PUBLICATIONS

European Search Report completed Mar. 4, 2015 for corresponding Application No. EP1419317.

(Continued)

*Primary Examiner* — William Levicky
(74) *Attorney, Agent, or Firm* — Notaro, Michalos & Zaccaria P.C.

(57) ABSTRACT

A catheter has an inflatable assembly at its distal portion, including a containment chamber, an axial core and a plurality of longitudinally oriented partitions extending from the axial core to the wall of the chamber to divide the containment chamber into at least four inflatable sectors. Hydraulic valves are connected to respective sectors to enable selective inflation of the sectors by a fluid when the valves are connected to a source of the fluid, and at least one surface electrode is mounted on each of the sectors. When introduced into a heart chamber and diametrically opposed sectors are inflated the assembly is stably fixed against the walls of the heart chamber and readings can be obtained from the surface electrodes of the inflated sectors.

2 Claims, 3 Drawing Sheets

(56) References Cited

U.S. PATENT DOCUMENTS

| | | |
|---|---|---|
| 2011/0254171 A1 | 10/2011 | Guo et al. |
| 2011/0276046 A1 | 11/2011 | Heimbecher et al. |
| 2012/0071870 A1* | 3/2012 | Salahieh ............ A61B 18/1492 606/33 |
| 2013/0172875 A1 | 7/2013 | Govari et al. |
| 2013/0184515 A1* | 7/2013 | Ovil et al. ........................ 600/17 |
| 2014/0276760 A1* | 9/2014 | Bonyak et al. ................... 606/34 |

FOREIGN PATENT DOCUMENTS

| | | |
|---|---|---|
| WO | 2010/018569 A1 | 2/2010 |
| WO | 2012/174375 A1 | 12/2010 |

OTHER PUBLICATIONS

Fellman, M. New Stretchable Electronics Device Promises to Make Cardiac Ablation Therapy Simpler, Evanston, IL., March 7, 2011.
Kim, DH et al. Materials for Multifunctional Balloon Catheters With Capabilities in Cardiac Electrophysiological Mapping and Ablation Therapy. Nature Materials. 2011;10(4):316-323.
Fellman, M., New Stretchable Electronics Device Promises to Make Cardiac Ablation Therapy Simpler, Evanston, IL., Mar. 7, 2011.
Kim, DH et al., Terials for Multifunctional Balloon Catheters with Capabilities in Cardiac Electrophysiological Mapping and Ablation Therapy, Nature Materials, 2011;10(4):316-323.
Sun, Y et al. Controlled Buckling of Semiconductor Nanoribbons for Stretchable Electronics, Nature Nanotechnology 1, 201-207(2006).

* cited by examiner

SEGMENTED BALLOON CATHETER

BACKGROUND OF THE INVENTION

1. Field of the Invention

This invention relates generally to methods and devices for invasive medical treatment. More particularly, this invention relates to improvements in catheters.

2. Description of the Related Art

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

One such catheter is proposed in PCT patent document WO 2012/174375. The catheter has a balloon that may be expanded at some portions along its length through inflation. The catheter may have one or more differently compliant sections along its length, or may have a generally noncompliant body with one or more separate compliant portions overlying it. The compliant portions may be separately inflated to create, in one section of the catheter an expanded disk-like configuration with a circular, somewhat planar surface that is oriented orthogonally to the direction of the guide wire and facing in a distal direction. The catheter bears one or more RF electrodes that are capable of conducting RF energy and may be positioned on the surface of the balloon such that they take a circular configuration on the planar surface.

SUMMARY OF THE INVENTION

There is provided according to embodiments of the invention a medical apparatus, including a catheter having an elongated shaft and a distal portion. The distal portion includes an inflatable assembly, wherein the inflatable assembly includes a containment chamber, an axial core and a plurality of longitudinally oriented partitions extending from the axial core to the wall of the chamber to divide the containment chamber into at least four inflatable sectors. The sectors are externally delimited by respective bounding portions of the outer surface. Hydraulic valves are connected to respective sectors to enable selective inflation of the sectors by a fluid when the valves are connected to a source of the fluid, and at least one surface electrode is mounted on each of the bounding portions.

The apparatus may include a tip electrode disposed on the catheter distal to the inflatable assembly.

According to another aspect of the apparatus, the outer surface has perforations formed therethrough for egress of the fluid from the containment chamber.

The apparatus may include a control processor operative to control the valves.

According to another aspect of the apparatus, the at least one surface electrode is deformable when their respective sectors inflate and deflate.

There is further provided according to embodiments of the invention a method of catheterization, which is carried out by introducing a catheter into a heart chamber of a subject. The distal portion of the catheter includes an inflatable assembly. The inflatable assembly includes a containment chamber, an axial core and a plurality of longitudinally oriented partitions extending from the axial core to the wall of the chamber to divide the containment chamber into at least four inflatable sectors. The sectors are externally delimited by respective bounding portions of the outer surface. Hydraulic valves are connected to respective sectors to enable selective inflation of the sectors by a fluid when the valves are connected to a source of the fluid, and at least one surface electrode is mounted on each of the bounding portions. The method is further carried out by inflating a selected one of the pairs of the sectors sufficiently to stably press the outer surface of the pairs of the inflated sectors against the walls of the heart chamber while avoiding inflation of others of the sectors, wherein the at least one surface electrode of each sector of the selected pair contacts the walls of the heart chamber.

Another aspect of the method is performed after inflating the selected pair of sector by measuring electrical potentials from the at least one surface electrode of the sectors of the selected pair. The method may include passing an electric current through at least one surface electrode to ablate a portion of the walls of the heart chamber.

One aspect of the method is performed after inflating the selected pair of sectors by deflating the selected pair of the sectors, and thereafter inflating another one of the pairs.

In a further aspect of the method the outer surface has perforations formed therethrough, wherein inflating comprises flowing the fluid through the valves into the selected pairs of the sectors. The method further includes controlling the valves to admit the fluid into the selected pair and to exclude the fluid from sectors other than the selected pair, and cooling a surface electrode of the selected pair during ablation of the selected pair by egressing the fluid from the containment chamber via the perforations.

According to still another aspect of the method, the members of the selected pair of the sectors are inflated concurrently.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

System Description

Figure 1:
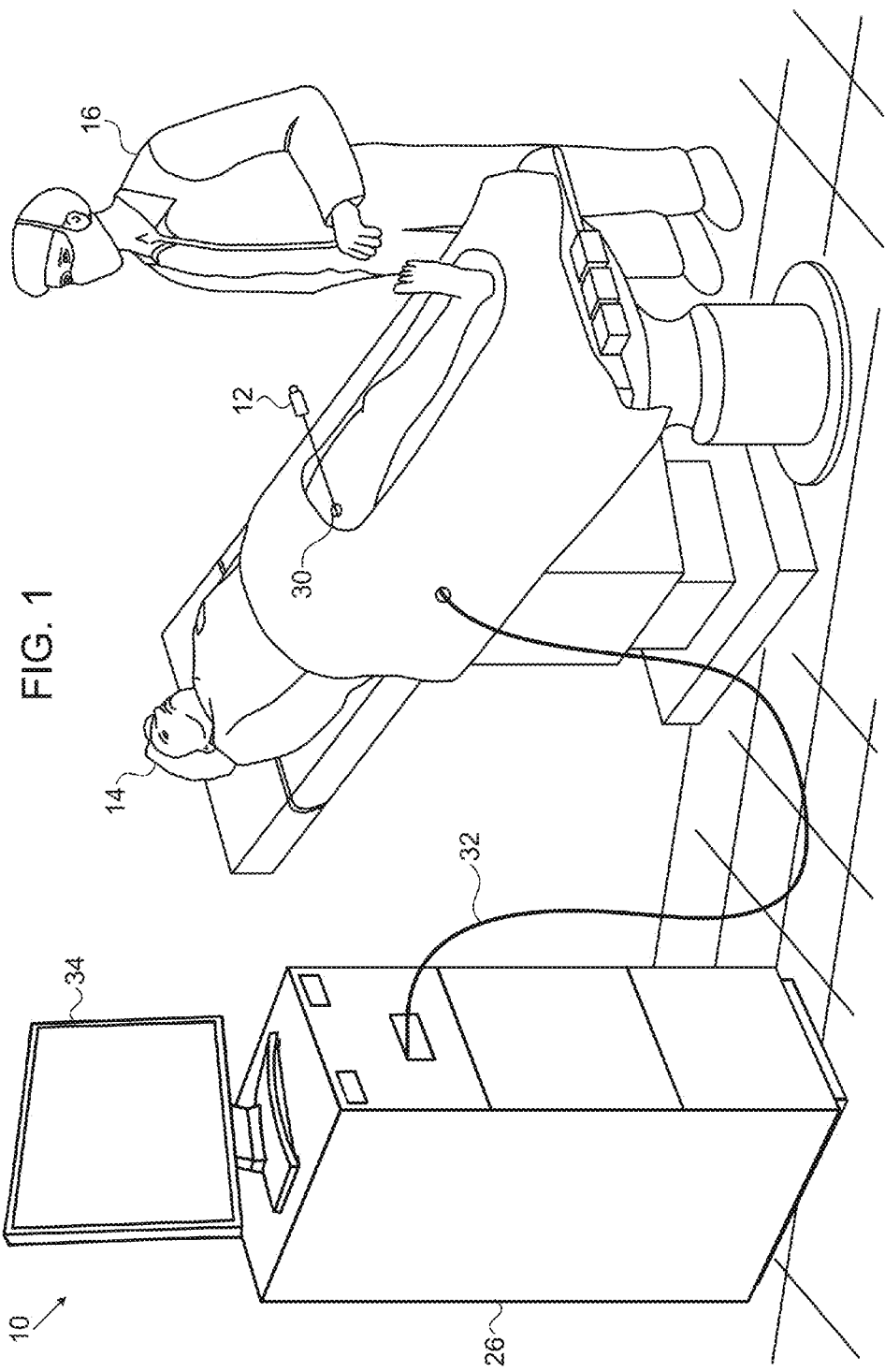
FIG. 1 is a schematic, pictorial illustration of a vascular catheterization system, in accordance with an embodiment of the present invention.

Turning now to the drawings, Reference is initially made to FIG. 1, which is a schematic, pictorial illustration of a vascular catheterization system 10 in accordance with an embodiment of the present invention. Use of the system 10 involves inserting a catheter 12 into the body of a subject 14 at an insertion point 30, for example a femoral artery or vein; thence into an internal body cavity, such as a heart chamber. Typically, the catheter 12 is used for diagnostic or therapeutic treatment performed by a medical practitioner 16, such as mapping electrical potentials in the heart or performing ablation of heart tissue. The catheter 12 may alternatively be used for other purposes, by itself or in conjunction with other treatment devices. Supporting elements related to the medical procedure are found in a control unit 26, which contains processors for data reported by signals from sensors in the catheter 12, e.g., via a cable 32. The control unit 26 may include an ablator power generator, irrigation pump and electrocardiographic circuitry. Events and data reported to the control unit 26 may be displayed on a monitor 34. However, as explained below, the control unit 26 need not include position-locating circuitry to track the location and orientation of the catheter 12 in the heart and elsewhere in the body of the subject 14. The catheter 12 typically contains hydraulic lines to transfer fluid from the irrigation pump via the catheter's handle to the distal portion of the catheter 12 as explained below. The hydraulic connection to the pump is not shown in FIG. 1 in order to preserve clarity of illustration.

Figure 2:
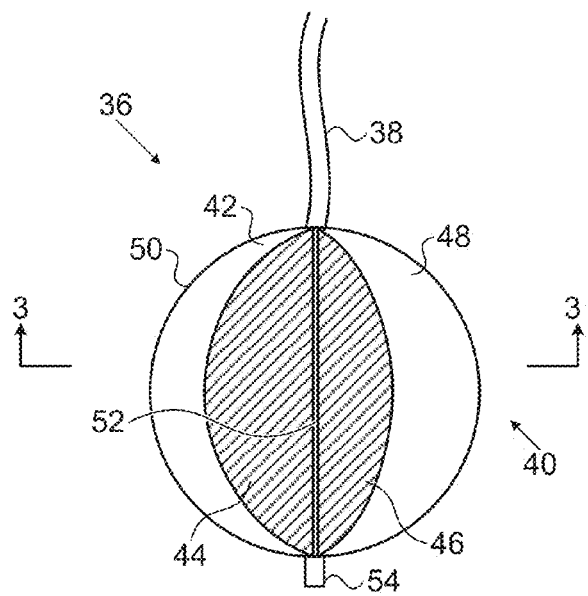
FIG. 2 is a longitudinal schematic view of the distal portion of a catheter in accordance with an embodiment of the invention.

Reference is now made to FIG. 2, which is a longitudinal schematic view of the distal portion of a catheter 36, which is useful for mapping regions in and around the heart and for tissue ablation in accordance with an embodiment of the invention. The catheter 36 comprises an elongated tubular shaft 38. An inflatable balloon assembly 40 is provided at the distal end of the catheter body. The inflatable balloon assembly 40 comprises a containment chamber, which is internally partitioned into sectors 42, 44, 46, 48 by a plurality of septa. The septa extend to an outer surface 50 from an axial core 52 and are oriented longitudinally about the axial core 52. The sectors 42, 44, 46, 48 are externally delimited by respective bounding portions of the outer surface 50. Although four sectors are shown in FIG. 2, the inflatable balloon assembly 40 may comprise any number of sectors greater than four. Surface features and functionality of the inflatable balloon assembly 40 are described below.

The sectors 42, 44, 46, 48 of the inflatable balloon assembly 40 must be flexible enough to maintain mechanical contact between the outer surface 50 and the wall of the heart chamber so that when inflated, they stably press the outer surface of the pairs of the inflated sectors against the wall of the heart chamber, but are not so rigid as to interfere with the movements of heart wall. The inflation pressure may be determined empirically by the operator, or may be determined using the teachings of U.S. patent application Ser. No. 13/343,024, entitled "Contact Assessment Based on Phase Measurement", Govari et al., now published as U.S. Patent Publication No. 2013/0172875, which is herein incorporated by reference.

The deflated sectors occupy little space and blood readily flows around them through the heart chamber, and thus blood flow through the heart is not substantially obstructed.

A tip electrode 54 can optionally be used for local measurements and ablation when the inflatable balloon assembly 40 is deflated.

Figure 3:
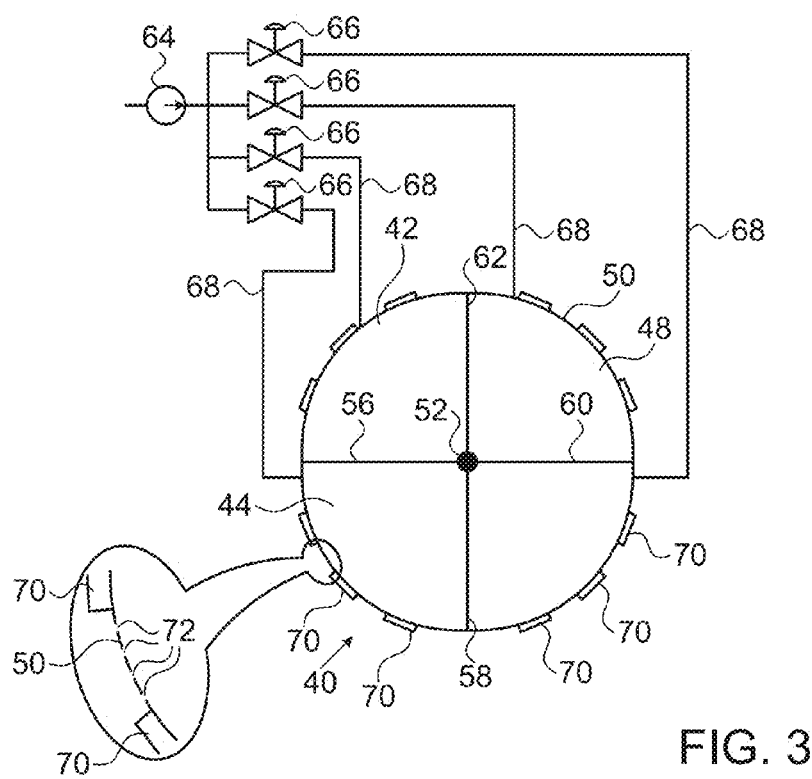
FIG. 3 is a schematic cross-sectional view of the catheter shown in FIG. 2 through line 3-3, in accordance with an embodiment of the invention.

Reference is now made to FIG. 3, which is a schematic cross-sectional view of the catheter 36 through line 3-3 of FIG. 2, in accordance with an embodiment of the invention. On this view, it can be appreciated that the inflatable balloon assembly 40 comprises a tubular structure comprising a preformed generally circular main region generally transverse and distal to the catheter body and having a circumferential outer surface 50. Septa 56, 58, 60, 62 extending radially from the core 52 to the outer surface 50 and define the sectors 42, 44, 46, 48.

Each of the sectors 42, 44, 46, 48 is independently connected to a fluid source 64, and is selectively inflatable using control valves 66, which deliver an irrigation fluid, typically saline, to the sectors 42, 44, 46, 48 via respective fluid lines 68. For example, sectors 44, 48, which oppose one another diametrically, are inflated concurrently, while the other sectors 42, 46 remain deflated. Fluid may be supplied to the sectors 44, 48 by simultaneously opening their respective control valves 66. In any case, both of the sectors 44, 48 become inflated in an operating position for taking measurements. The control unit 26 (FIG. 1) may comprise a processor to regulate the control valves 66. Alternatively, the control valves 66 may be controlled manually by the practitioner 16 or an assistant.

The portion of the outer surface 50 overlying respective sectors 42, 44, 46, 48 has a flexible array of electrodes 70 mounted thereon, which can be used for mapping and ablation. The electrodes 70 and associated connectors are required to deform as the sectors 42, 44, 46, 48 expand and contract. Construction of flexible, stretchable electronic elements is known, for example from the documents Controlled Buckling of Semiconductor Nanoribbons for Stretchable Electronics, Yugang Sun et al., Nature Nanotechnology 1, 201-207 (2006) and U.S. Patent Application Publication No. 2011/0254171. Devices constructed in such manner are capable of conforming to curved surfaces and withstanding mechanical deformations.

Optionally, perforations 72 may be formed through the outer surface 50 near the electrodes 70. In such case, the fluid selectively delivered to the sectors 42, 44, 46, 48 from the fluid source 64 egresses the inflatable balloon assembly 40 via the perforations 72 and cools the electrodes 70 and the ablation site during ablation.

Operation

Figure 4:
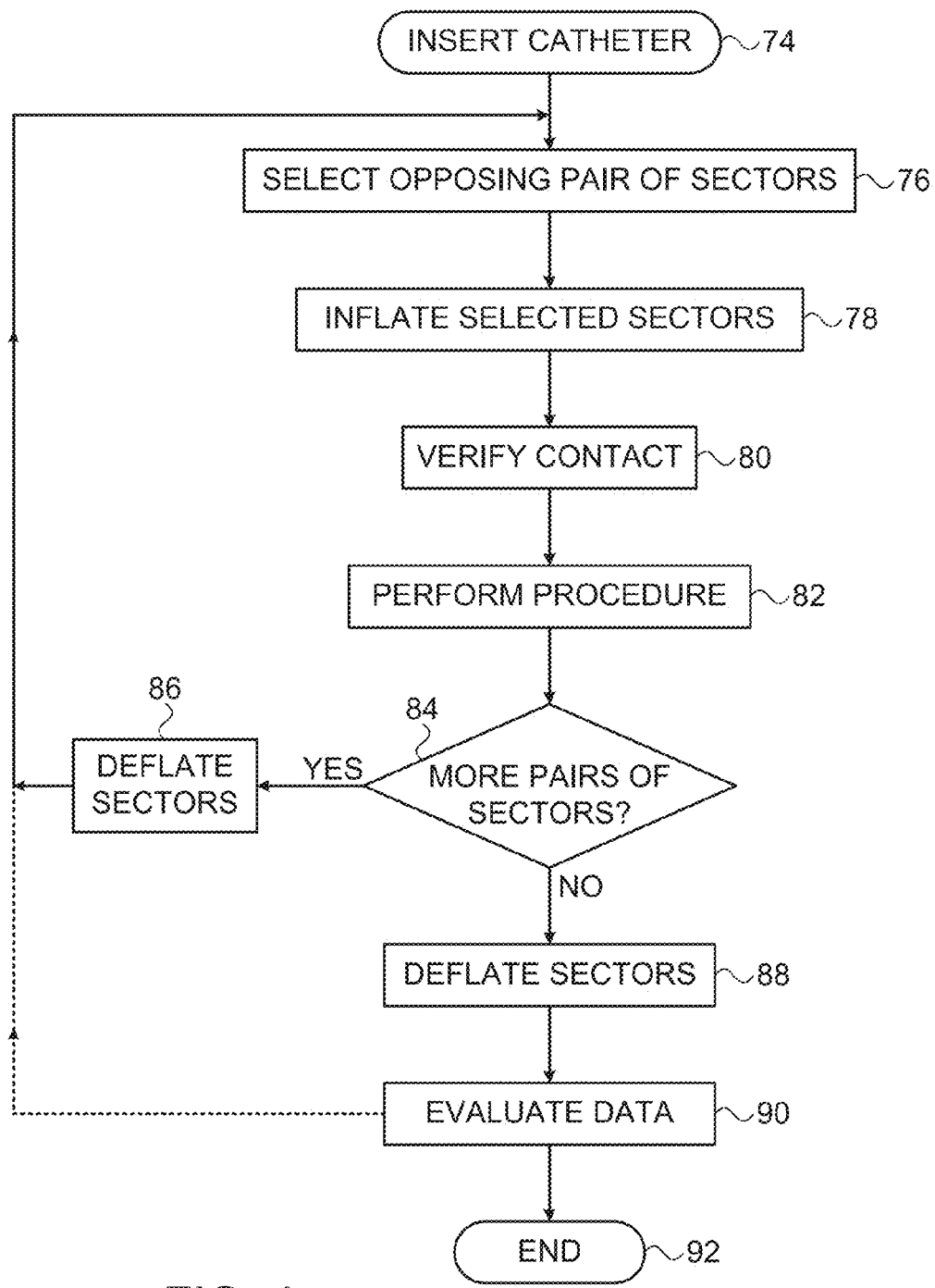
FIG. 4 is a flow chart of a method of cardiac catheterization using a segmented balloon catheter, in accordance with an embodiment of the invention.

Reference is now made to FIG. 4, which is a flow chart of a method of cardiac catheterization using a segmented balloon catheter, in accordance with an embodiment of the invention. Not all illustrated process steps may be required to implement the process. At initial step 74 the catheter 36 (FIG. 2) is inserted into the heart in a known manner, and positioned within a chamber of interest. At this point the sectors 42, 44, 46, 48 are all deflated.

Next, at step 76, a diametrically opposing pair of sectors is selected, for example the sectors 44, 48 (FIG. 3).

Next, at step 78, the pair of sectors selected in step 76 are inflated. All non-selected sectors remain deflated.

Next, at step 80, electrical contact between the wall of the cardiac chamber and those electrodes 70 that are mounted on the selected sectors is verified.

Next, at step 82 a measurement or procedure is performed using the electrodes 70 of the two opposing inflated sectors, for example bipolar measurements of electrical potentials during the cardiac cycle.

Next, at decision step 84, it is determined if more pairs of sectors of the inflatable balloon assembly 40 remain to be processed. If the determination at decision step 84 is affirmative, then control proceeds to step 86. The current pair of inflated sectors is deflated. Control returns to step 76 to iterate the procedure with another pair of sectors.

If the determination at decision step 84 is negative then at step 88 the current pair of inflated sectors is deflated. This could occur if all pairs have been inflated, or if it was decided to evaluate the signals obtained from fewer than all pairs of sectors. Indeed, it may be appropriate to evaluate the signals obtained from one pair of sectors before inflating the next pair. At step 90, signals thus far collected from the endocardial surfaces via the electrodes of the pairs of inflated sectors are evaluated, either by the physician or automatically.

After evaluating the ECG signals, as indicated by a broken line, selected pairs of sectors may optionally be reflated, and control would then return to step 76. Alternatively, the physician typically makes a decision regarding ablation at final step 92.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A medical apparatus, comprising:
a catheter having an elongated shaft and a distal portion, the distal portion comprising an inflatable assembly,
wherein the inflatable assembly comprises a containment chamber having an outer wall, an outer surface, an axial core and a plurality of longitudinally oriented partitions extending from the axial core to the outer wall to divide the containment chamber into at least four inflatable sectors, the sectors being externally delimited by respective bounding portions of the outer surface, the outer surface having perforations formed therethrough;
hydraulic valves connected to respective sectors to enable selective inflation of diametrically opposed sectors by a fluid when the valves are connected to a source of the fluid;
at least one surface electrode mounted on each of the bounding portions, the at least one surface electrode being deformable, the at least one surface electrode being adapted to receive an electric current and ablate a portion of a heart chamber wall; and
a tip electrode disposed on the catheter distal to the inflatable assembly, the tip electrode adapted to provide measurements and further adapted to ablate a portion of a heart chamber wall, and
a control processor operative to control the valves,
wherein the apparatus is adapted to provide verification of electrical contact between the heart chamber wall and electrodes of diametrically opposed sectors.

2. A medical apparatus, comprising:
a catheter having an elongated shaft and a distal portion, the distal portion comprising an inflatable assembly,
wherein the inflatable assembly comprises a containment chamber having an outer wall, an outer surface, an axial core and a plurality of longitudinally oriented partitions extending from the axial core to the outer wall to divide the containment chamber into at least four inflatable sectors, the sectors being externally delimited by respective bounding portions of the outer surface, the outer surface having perforations formed therethrough;
hydraulic valves connected to respective sectors to enable selective inflation of diametrically opposed sectors by a fluid when the valves are connected to a source of the fluid;
at least one surface electrode mounted on each of the bounding portions, the at least one surface electrode being deformable, the at least one surface electrode being adapted to receive an electric current and ablate a portion of a heart chamber wall; and
a tip electrode disposed on the catheter distal to the inflatable assembly, the tip electrode adapted to provide measurements and further adapted to ablate a portion of a heart chamber wall,
a control processor operative to control the valves, the control processor being adapted to control the valves to admit the fluid into a selected pair of diametrically opposed sectors and to exclude the fluid from sectors other than the selected pair of diametrically opposed sectors, the control processor adapted to cool at least one surface electrode of the selected pair of diametrically opposed sectors by egress of the fluid from the containment chamber via the perforations,
wherein the apparatus is adapted to provide verification of electrical contact between the heart chamber wall and electrodes of diametrically opposed sectors.

* * * * *